US00PP14118P39

(12) United States Plant Patent
Cosner

(10) Patent No.: US PP14,118 P3
(45) Date of Patent: Sep. 2, 2003

(54) LOTUS VINE PLANT NAMED 'TIGO'

(75) Inventor: Harlan B. Cosner, Broadbent, OR (US)

(73) Assignees: Harlan Cosner, Rogue River, OR (US); Sue Cosner, Rogue River, OR (US)

( * ) Notice: Subject to any disclaimer, the term of this patent is extended or adjusted under 35 U.S.C. 154(b) by 0 days.

(21) Appl. No.: 09/826,501

(22) Filed: Apr. 4, 2001

(65) Prior Publication Data

US 2002/0148020 P1 Oct. 10, 2002

(51) Int. Cl.[7] ..... A01H 5/00
(52) U.S. Cl. ..... Plt./226

(58) Field of Search ..... Plt./226

(56) References Cited

U.S. PATENT DOCUMENTS

PP10,864 P * 4/1999 Cosner et al. ..... Plt./226
PP10,868 P * 4/1999 Cosner et al. ..... Plt./226

* cited by examiner

*Primary Examiner*—Kent Bell
(74) *Attorney, Agent, or Firm*—Bradley M. Ganz; Ganz Law, P.C.

(57) ABSTRACT

A new and distinct cultivar of (*Lotus berthelotii*×*Lotus maculata*)×*Lotus maculata* plant named 'TiGo', characterized by its pendulous growth habit and pan-seasonal production of yellow-red flowers.

1 Drawing Sheet

Figure 1:
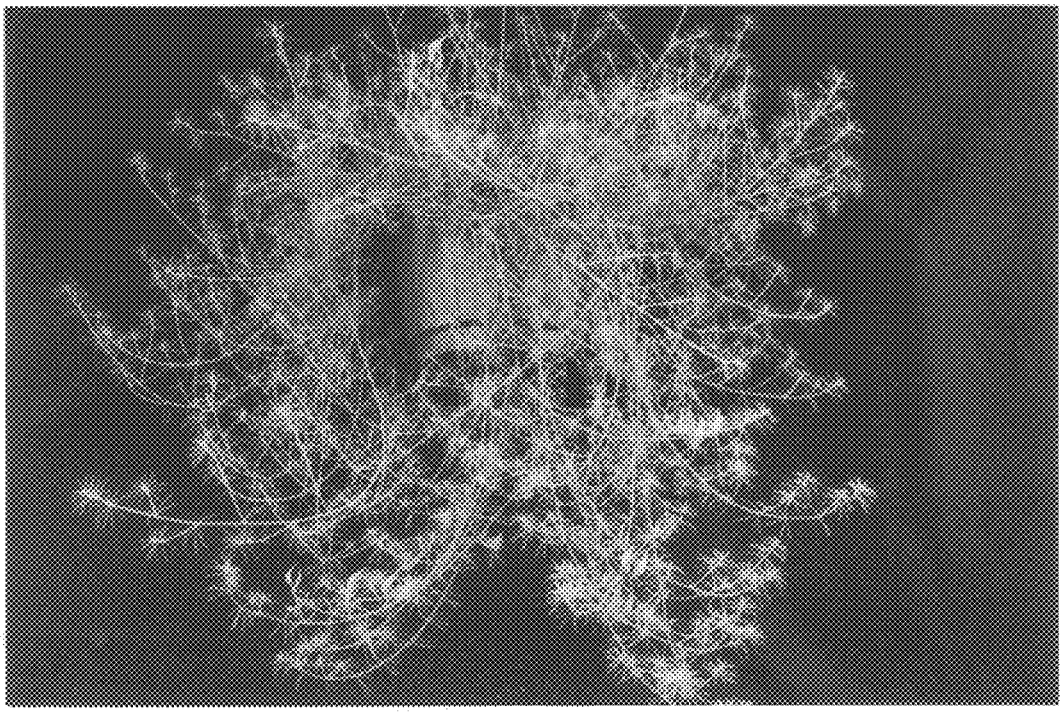

The present invention is directed to a new and distinct cultivar botanically known as pan-seasonal (*Lotus berthelotii*×*Lotus maculata*)×*Lotus maculata* relating to U.S. patent application Ser. No. 09/545,234 filed Apr. 7, 2000, entitled "Pan-Seasonal Lotus Vine Plant and Methods of Breeding and Propagating the Same", from which priority is claimed. Application Ser. No. 09/545,234 is hereby incorporated by reference for all it discloses, as if it were set forth herein in its entirety.

BACKGROUND OF THE INVENTION

Field of Invention

The present invention relates to a new and distinct cultivar botanically known as (*Lotus berthelotii*×*Lotus maculata*)× *Lotus maculata* and hereinafter referred to by the cultivar name 'TiGo'.

The cultivar of the accompanying photograph was developed and selected in a controlled breeding program in Coquille, Oreg., by the inventor, Harlan Cosner, as described herein.

The plant is intended primarily to be ornamentally used in, for example, hanging baskets, in colder regions of the United States, and possibly as ground cover in regions of warmer winters, with minimum temperatures above 25° F.

Description of the Relevant Art

'TiGo' is a result of a cross between a *Lotus berthelotii*× *Lotus maculata* and a *Lotus maculata.* The pollen parent was 'Amazon Sunset-A', of pending U.S. patent application Ser. No. 09/545,234 filed Apr. 7, 2000, entitled "Pan-Seasonal Lotus Vine Plant and Methods of Breeding and Propagating the Same". The seed parent was an unnamed yellow *Lotus maculata* seedling.

The seed parent was of similar color, but it did not flower unless it received a vernalization period of at least 30 days of minimum temperatures below 40° F. It then flowered for about 45 consecutive days. Flowering then ceased again until it was again vernalized. The instant plant does not require vernalization, and flowers continuously as long as the minimum temperature remains below 65° F. Flowering may decrease if the minimum temperature exceeds 65° F. Flowering may also decrease in possible photoperiodic reaction to winter short dull days.

The primary difference between the pollen parent and the instant plant is in flower color, the flowers of the instant plant appear yellow when observed at a distance of a few feet while the flowers of the pollen parent appear scarlet or red.

The instant plant was discovered as a seedling from a controlled cross-pollination made by the inventor under greenhouse conditions. The plant was produced in a controlled breeding program at Coquille, Oreg. First asexual production was completed in Coquille, Oreg. at least as early as Aug. 5, 1998.

Asexual propagation of the cultivar by lateral or apical stems with leaves has proven the plant to be stable in successive generations.

Color references are according to The Royal Horticultural Society Colour Chart, except where general terms of ordinary dictionary significance are used.

SUMMARY OF THE INVENTION

A new and distinct cultivar of (*Lotus berthelotii*×*Lotus maculata*)×*Lotus maculata* having a pendulous plant habit and pan-seasonal production of yellow-red bi-color flowers, which appear yellow from a distance of a few feet. "Pan-seasonal" refers to instant plant's ability to produce flowers throughout the year in most climate zones.

DESCRIPTION OF THE PHOTOGRAPHS

FIG. 1. depicts a side perspective view of a typical plant of 'TiGo'.

Figure 2:
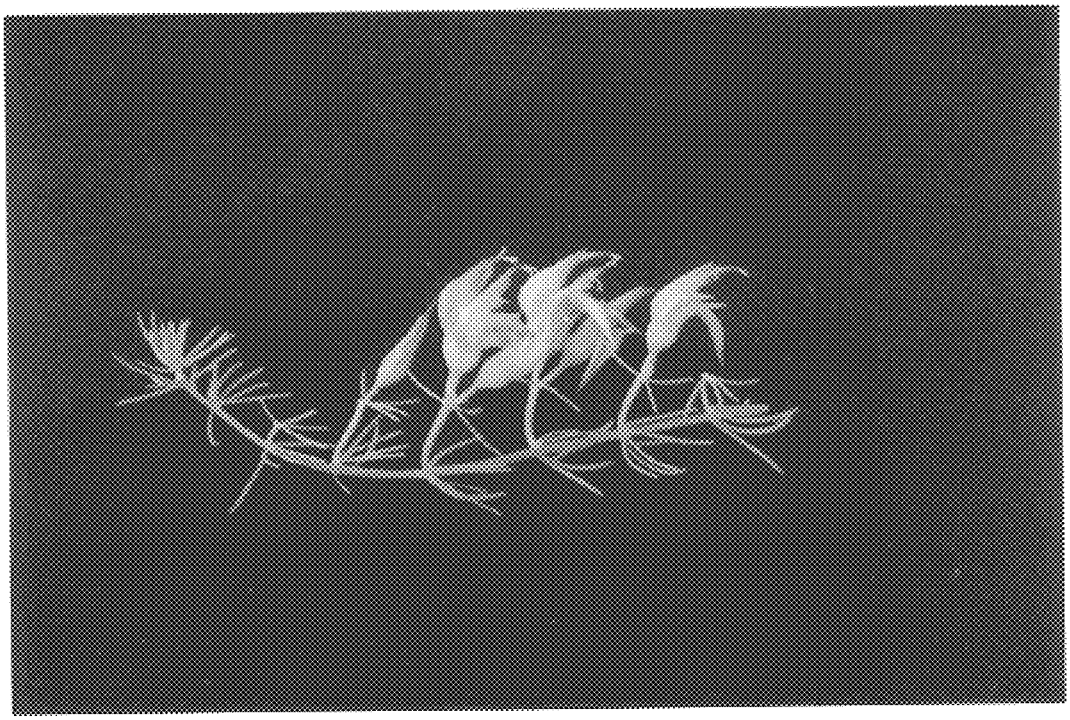

FIG. 2. depicts a close up view of typical flowers and leaves of 'TiGo'.

PLANT DESCRIPTION

The following observations, measurements and description of the plant and flowers are based on the following environment and cultural practices at Coquille, Oreg. The following measurements, values and comparisons describe plants about 14 weeks from a rooted cutting or 18 weeks from an unrooted cutting, as represented by the plants of FIGS. 1 and 2. The plants were grown under a double layer of polyethylene film with a 40% shade cloth over the top of a greenhouse, with temperatures ranging from between 60° F. to 68° F. at night, and between 85° F. to 100° F. during the daytime. The individual plants were grown in 10-inch hanging baskets in a soiless medium consisting of Perlite and peat moss. Plants were liquid fed with 20-10-20 plus minor elements. The cutting types were lateral or apical stems. Cuttings were stuck in about the first week of June 2000 and finished in about late October 2000. Light levels were a maximum of 1,000–6,000 ft. candles, depending on cloud cover.

The plant of the present invention has not been observed in all possible environmental and/or cultural conditions. The phenotype may vary significantly with variations in environment such as temperature, light level, humidity and also with cultural practices such as fertility, soil and water quality.

The accompanying photographs illustrate the overall appearance and the flower color of the cultivar of the present invention described herein. The photographs were taken of a mature plant during early inflorescence.

There may be variations between the colors in the photograph and the colors in the following description due to, for example, light reflectance, the amount of blue or red light captured in the film, and/or propagation stress. If such variations occur, then the written description shall control.

The following description was taken of the 'TiGo' cultivar shown in the photographs.

Parentage: The new cultivar was developed by standard cross-pollination. As noted above, its pollen parent was an 'Amazon Sunset-A', and the seed parent was an unnamed yellow *Lotus maculata* seedling.

Propagation:

*Type of cutting.*—Lateral or apical stems with leaves.

*Time to initiate roots.*—Approximately 12 to 14 days at 70° F. soil temperature, and 70° F. air temperature, with radiant heat applied at the bench top or just below the rooting medium. Winter low light conditions may require longer time to initiate roots.

Appearance and form of mature plant:

*Plant form and habit.*—Plant is free branching and pendulous.

*Plant size.*—Stems generally protrude upwards from the base of the plant, which is generally at or near soil level, until they reach about 30 cm. in length, then they become pendulous. Stem length at first flowering is generally about 50 cm. Plant width is 100 cm. Both of these measurements are a function of age, the above environmental and cultural practices, and can vary accordingly. Plants generally mature in about 14 weeks from a rooted cutting or 18 weeks from an unrooted cutting, this can vary depending on the stage of maturity of the mother plant when the cuttings are taken.

*Rooting habit.*—Roots are coarse and somewhat stringy.

*Branching habit.*—Pendulous.

*Stems.*—Habit is pendulous. Internode length on mature stems is about 3 cm. Lateral stems alternate along the main stem. Color does not match any in the chart, but is closest to 139D on all surfaces when juvenile. With age, the surfaces of the stems that are the most exposed to light become densely spotted with a reddish brown color making the color appear close to 200D. The undersurfaces or shaded surfaces tend to remain close to 139D.

*Foliage.*—Shape is linear. Leaves usually numbering 6 or 7 appear in half whorls that alternate in position along the stems.

*Foliage size.*—Size of the largest leaves is about 1.5 cm. in length, and 1 mm. in width.

*Foliage color.*—Adaxial surface color is 138A and the abaxial surface color is 138B. There is no visible venation. Juvenile foliage adaxial surface color is 138A and the abaxial surface color is 138B. There is no visible venation.

*Foliage texture.*—The foliage texture is smooth with tiny pubescence.

*Petioles.*—There appears not to be any petioles, or if there are any, they are too short to determine, as the leaves appear to be attached directly to the stems.

*Flower habit.*—Outward away from stems.

*Flower size shape.*—Flowers are not round, but are ovular and are about 0.7 cm. across the narrow direction and are about 1 cm across the wider direction; and about 3 cm. long, and about 1 cm. deep. Each of the fused center petals are about 0.8 cm. wide and 2.7 cm. deep, and the shape is linear on one side, and ovate on the other with exaggerated and curved acuminate apex (more like a curved, tapering, acicular or filliform apex), entire margin and cuneate base. Each side petal is about 0.7 cm. wide and 2.25 cm. long, and the shape is linear on one side, and ovate on the other side, with a cuneate base and acuminate apex, and entire margin. The center petal is about 0.5 cm. wide and 2.5 cm. long that is strongly reflexed into a U-shape, cuneate base, strongly acuminate apex, and entire margin. These measurements refer to the larger flowers.

*Flower texture.*—Smooth.

*Flower count.*—Usually 3 or 4 flowers per axial.

*Flowers borne.*—Arising from leaf axils, one peduncle per node, with generally one to four pedicels per peduncle, each pedicel producing a single flower. Flowers are single in type.

*Natural flowering season.*—Year around under greenhouse conditions, except flowering may decrease or cease during low-light periods of winter, indicating the plant may be somewhat photoperiodic. No vernalization is required and the plants flower continuously when minimum temperatures are below 65° F., except possible photoperiodic responses as stated above. The plant also flowers continuously at sustained minimum temperatures in excess of 65° F., except to a lesser extent.

*Time to flower.*—About 12 weeks from rooted cutting to first inflorescence, depending on the age of the cuttings that were stuck, and other environmental conditions. Budded cuttings flowered earlier than juvenile cuttings.

*Flower shape and color.*—There are 5 petals, with the two largest petals fused together at each side forming a hollow tube-type of single organ that is wider at the base than at the apex. The adaxial surface of each of these petals is close to 11C at the base and the apex appears close to 180A to 180B, but is hard to determine as the petals roll up when separated from each other. There are two side petals which parallel the main two fused petals, their adaxial surface is close to 12A at base, 14A from about midway between base and apex to apex, and there are reddish streaks toward the apex which are very narrow, making the color hard to determine, but which appear close to 179A to 180A. There is a strongly reflexed center petal which attaches to the calyx and covers about half of the abaxial surface of the two side petals, the adaxial surface color is closest to 14B on the edges that extends from a base of 9D to about three-fourths of the way to the apex. There is a strip that does not match any color in the chart, which is darker than 187A but not as dark as 200A that is in the center of the petal.

*Abaxial surface.*—The abaxial surface of the outer fused petals is close to 31 B to 31 C at the base for about half a centimeter towards apex, then a strip up to extending to about the middle of close to 12A with tiny reddish veins too narrow to determine that extend from the remaining apical portion of the petals into the 12A portion. The apical portion of the petal, which is about half the petal length, is colored 171A. The side petals at the base are close to 37B for about half a centemeter on the side opposite the reflexed petal, the remaining portion of the petals, except the apex, are closest to 13A. There are tiny reddish streaks that are too small to determine that extend from the apex about a centemeter into the 13A coloring with the apex color appearing the same as the tiny streaks, which is closest to 179A. The reflexed center petal has about a half centemeter of a base color of close to 1C then there is a small strip of 179A on each outer edge. Inside that spot, on each side, is a small spot of close to 164A, then there is a strip of close to 163A on the outer edges (extending from the spot of 179A to about three-quarters of the petal length toward the apex) with very narrow stripes of a reddish color, which appears close to 180A. There is a center stripe close to 166A, and the apex appears close to 175A.

*Flower buds.*—Lanceolate in shape, 1.5 cm. in length and 0.4 cm. in diameter at the base. Buds prior to opening are close to 145C at the base, and 147C toward the apex.

*Peduncles.*—Length is about 1.8 cm. and diameter is about 1.5 mm. The color does not match any in the chart, but appears between 145B and 145C with extremely tiny reddish spots, which are too small to determine color.

*Pedicels.*—About 0.8 cm. long and about 1 mm. in width. Color is closest to 145B.

*Calyx.*—There is one calyx measuring about 0.6 cm. wide and 1.25 cm. long. It is sheathing and crown-like in shape with five pointed lobes, each with an acute to acuminate apex. There are two which are longer than the other three. These longer two are curved and follow the curvature of the center reflexed petal described above. The apex of each of the shorter three points is about 0.6 cm. long and the longer two are each about 1 cm. long. The adaxial surface is close to 144C at the base, and close to 138B at the apex. The abaxial surface is 144B to 144C at the base and 138B at the apex. There is very fine pubescence on both surfaces.

*Reproductive organs.*—There is one pistil, ovary is colored 145A, about 1.5 cm. in length and 1 mm. in diameter. The stigma is colored close to 153D, about: 0.5 mm. wide and 2.5 cm. long. The stamen is a single organ at the base which sheaths the ovary, then it splits into 10 individual filaments, each of which produces a tiny anther that appears close to 153A, but exact color cannot be determined due to the tiny size of the anthers. The stamen and filaments are colored close to 150C. The pollen color appears close to 11C. The pollen is shed before the stigma is receptive to pollen and natural seed production has not occurred.

*Disease resistance.*—Plants seem to be highly resistant or even immune to INSV (Impatiens Necrotic Spotted Wilt Virus), TSWV (Tomato Spotted Wilt Virus) and most other viruses, bacteria and fungi. Plants have been tested in outdoor unscreened conditions where obvious virus contaminations were prevalent and thrip populations were high, but no occurrences of virus contaminations were noticed despite high populations of thrips on the plants in close proximity to plants of other species susceptible to such contaminations, and showing obvious virus symptoms.

*Rooting ability.*—Easy, no hormones needed.

*Cold/heat resistance.*—Plants have flowered continuously under temperatures where maximums exceeded 100° F., and where minimums did not fall below 65° F.

COMPARISON CHART TO PRIOR ART

The cultivar has only been compared to the parents and the comparison is indicated above.

It is claimed:

1. A new and distinct variety of (*Lotus berthelotii*×*Lotus maculata*)×*Lotus maculata* plant named 'TiGo', as illustrated and described herein.

* * * * *